United States Patent
Hu et al.

(10) Patent No.: US 11,524,148 B2
(45) Date of Patent: Dec. 13, 2022

(54) BALLOON CATHETER FLOW DEVICE

(71) Applicant: UNIVERSITY OF MARYLAND, BALTIMORE, Baltimore, MD (US)

(72) Inventors: Bingren Hu, Baltimore, MD (US); Chunli Liu, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 654 days.

(21) Appl. No.: 16/467,431

(22) PCT Filed: Dec. 6, 2017

(86) PCT No.: PCT/US2017/064880
§ 371 (c)(1),
(2) Date: Jun. 6, 2019

(87) PCT Pub. No.: WO2018/106788
PCT Pub. Date: Jun. 14, 2018

(65) Prior Publication Data
US 2021/0290916 A1    Sep. 23, 2021

Related U.S. Application Data

(60) Provisional application No. 62/430,612, filed on Dec. 6, 2016.

(51) Int. Cl.
*A61M 29/00* (2006.01)
*A61M 25/10* (2013.01)
*A61M 25/00* (2006.01)

(52) U.S. Cl.
CPC .... *A61M 25/104* (2013.01); *A61M 25/10185* (2013.11); *A61M 2025/0001* (2013.01);
(Continued)

(58) Field of Classification Search
CPC .. A61M 2025/0001; A61M 2025/1015; A61M 2025/1095; A61M 2025/0175; A61M 2025/1052; A61M 25/1011
See application file for complete search history.

(56) References Cited

U.S. PATENT DOCUMENTS

| 6,083,198 A | 7/2000 | Afzal |
| 7,780,628 B1 | 8/2010 | Keren et al. |

(Continued)

FOREIGN PATENT DOCUMENTS

WO    2013/142386    9/2013

OTHER PUBLICATIONS

International Search Report issued in corresponding International Patent Application No. PCT/US17/64880 dated Feb. 22, 2018.

*Primary Examiner* — Rebecca E Eisenberg
(74) *Attorney, Agent, or Firm* — Whiteford, Taylor & Preston, LLP; Gregory M. Stone

(57) ABSTRACT

Disclosed is an inter- and intra-catheter flow device for the management of vascular bleeding disorders that provide a liquid flow-pass between proximal and distal balloons for bridging the circulation between the upper and lower segments of a hemorrhaging artery or blood vessel, while blocking the blood flow to the hemorrhaging middle segment(s) of the artery or blood vessel between the two or more balloons. When only one balloon is inflated, these devices can create a pressure gradient between proximal or distal and middle segments of the artery or blood vessel. These devices are useful for controlling proximal artery blood pressure, preventing distal ischemia-reperfusion injury, identifying the bleeding location, controlling the bleeding, repairing and remodeling vascular structures, (Continued)

extending resuscitative endovascular balloon occlusion of the aorta (REBOA) use duration, and performing fluid resuscitation.

20 Claims, 6 Drawing Sheets

(52) U.S. Cl.
CPC ............ *A61M 2025/1015* (2013.01); *A61M 2025/1095* (2013.01)

(56) References Cited

U.S. PATENT DOCUMENTS

2002/0169413 A1\* 11/2002 Keren ................ A61M 1/3659
    604/101.03
2009/0054922 A1\* 2/2009 Broker ............. A61M 25/1002
    606/194
2012/0259215 A1\* 10/2012 Gerrans ............ A61M 25/1011
    600/435

\* cited by examiner

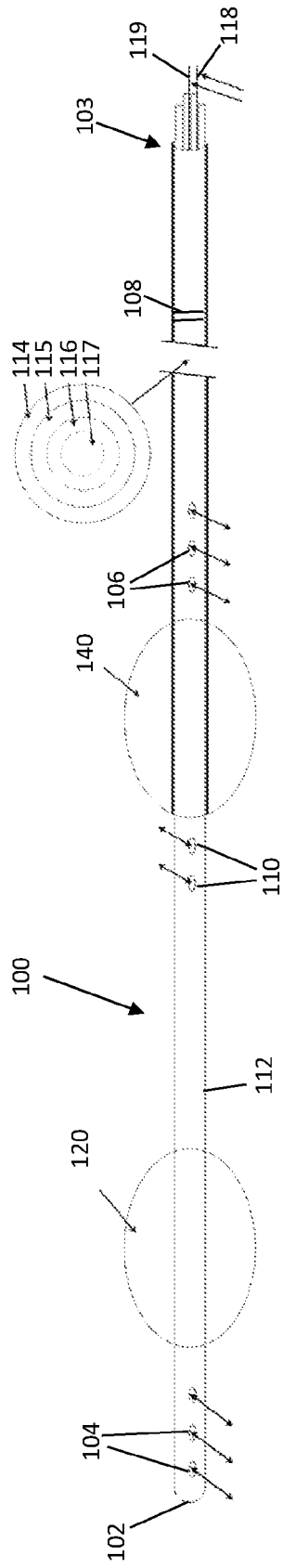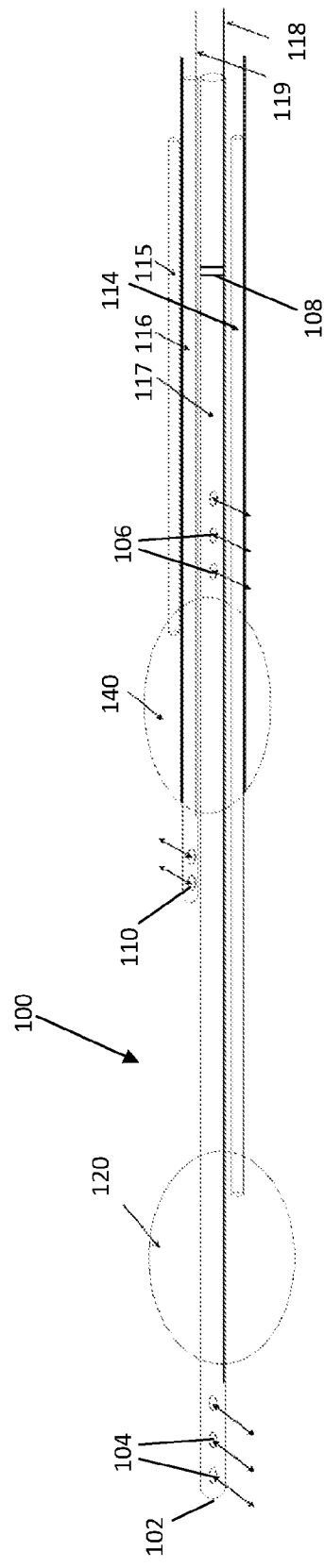

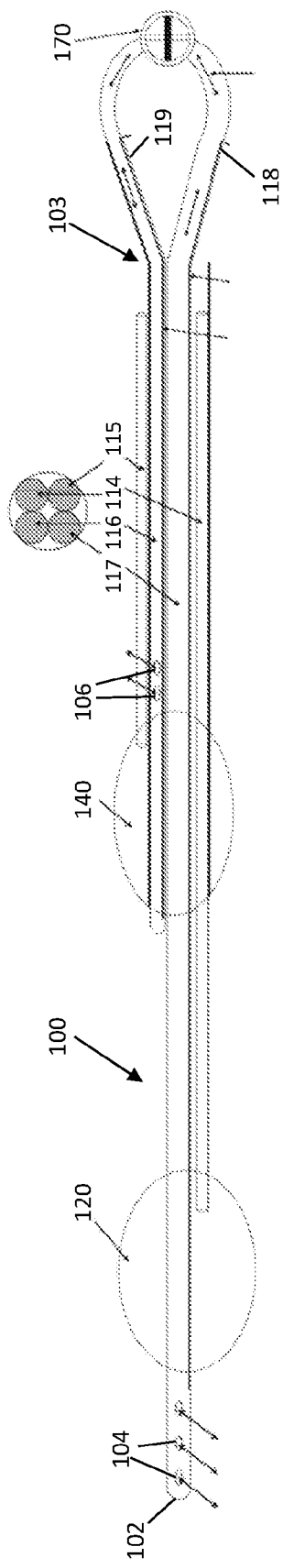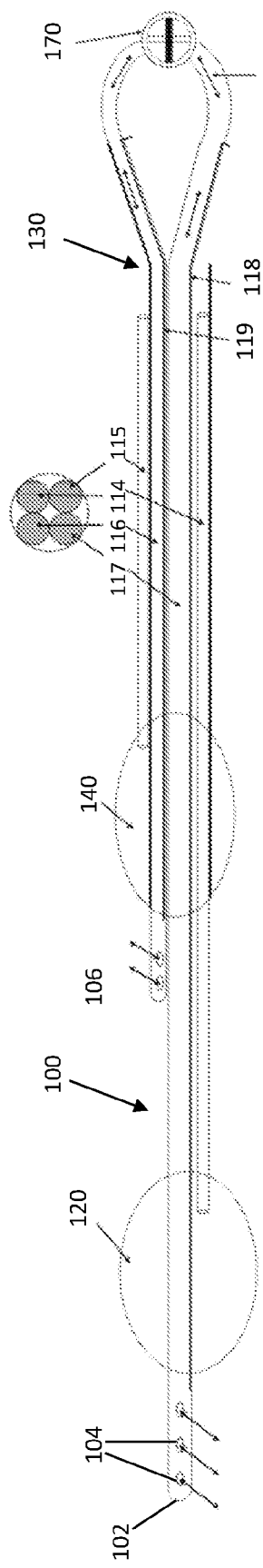

BALLOON CATHETER FLOW DEVICE

FIELD OF THE INVENTION

The present invention relates generally to devices to treat, control or manage vascular bleeding disorders, and more particularly to devices for managing blood flow after hemorrhage, as may be caused by several medical conditions, including but not limited to a serious bodily injury, operating room surgical procedure, organ transplantation, and artery aneurysm.

BACKGROUND OF THE INVENTION

Hemorrhage or bleeding is a significant cause of death for warfighters injured in combat, and for surgical patients in the operating room. Emergency medical intervention in such environments is often of limited success, particularly in those cases in which an individual has suffered an injury causing non-compressible torso hemorrhage. Resuscitative endovascular balloon occlusion of the aorta (REBOA) is a technique that has been used in attempts to block the blood flow to the hemorrhage territory, thus providing an opportunity for hemorrhagic patients to develop definitive hemostasis, in turn allowing operators to repair the site of the hemorrhage. In fact, the concept of REBOA was introduced over 50 years ago for controlling lethal hemorrhage of injured Korean War soldiers, but with limited success.

With the development of modern endovascular materials and devices, as well as modernized vascular surgical methodologies, the inventors herein believe that REBOA presents significant opportunity for enabling the control and repair of lethal hemorrhage, and more particularly that REBOA may significantly improve the medical operator's ability to manage patients suffering from hemorrhagic shock due to traumatic injuries in non-compressible areas of the body such as the chest, abdomen, or pelvis, commonly and collectively known as non-compressible torso hemorrhage (NCTH). NCTH is defined as vascular disruption to the axial torso vessels, solid organs, pulmonary parenchyma or the bony pelvis, accompanied by shock, and has a mortality of approximately 45%.

Unfortunately, the use of REBOA is significantly limited by the distal ischemia-reperfusion and rebound hypotension upon deflation of the balloon. As a result, clinical data show that the limitations of REBOA have thus far tended to overweigh the benefits in several large-scale clinical retrospect studies. These limitations significantly restrain the therapeutic implementations of this advanced and less invasive REBOA in many clinical settings.

To overcome these limitations, several strategies have been tested. One is to use partial REBOA that permits a controlled amount of distal perfusion while maintaining proximal aortic pressure, thus extending the time window of REBOA use for endovascular hemorrhage control. Another strategy is to use a hybrid endovascular-extracorporeal circuit variable aortic control (EVAC) device that bypasses the segment just below the balloon occlusion, thus creating a pressure ladder or gradient between the proximal and distal artery. This strategy can extend REBOA use duration in a lethal animal model of hemorrhagic shock. However, these strategies are yet to be further developed and widely adopted.

It would therefore be advantageous to provide improved devices and methods that would allow stoppage or reduction of blood flow to the site of a hemorrhage (and particularly an NCTH), in turn maintaining proximal aortic pressure, but that would still allow blood flow to the vascular system past the point of such hemorrhage.

SUMMARY OF THE INVENTION

The present invention discloses, in accordance with aspects of an embodiment of the invention, a balloon flow REBOA catheter configured to allow blood flow from a proximal segment of the artery to the distal segment of such artery experiencing hemorrhage. In certain embodiments, the balloon flow REBOA catheter comprises a catheter body and at least one inflatable balloon positioned on the exterior of the catheter body. The catheter includes at least one inlet port that may receive blood from the proximal segment of the patient's artery, and may channel blood through the catheter to one or more perfusion ports positioned on an opposite side of the inflatable balloon from the inlet port, in turn causing the flow of blood to either bypass the hemorrhagic site or reduce and otherwise control the flow of blood at the hemorrhagic site, thus allowing an operator additional time to repair the hemorrhage. In certain configurations disclosed herein, two balloons may be provided on the catheter body, wherein blood may flow from a proximal segment of the artery into the one or more inlet ports at the distal end of the catheter, through the catheter body and exit the catheter through the perfusion ports in the distal segment of the artery (distal in the patient's artery to the position of the second balloon on the catheter), with the middle segment of the catheter positioned between the two balloons carrying blood while preventing some or all blood flow to the specific site of the hemorrhage. In other configurations disclosed herein, a moveable plunger or other flow restricting and/or regulating devices may be provided within the catheter which may regulate flow to and through the perfusion ports. Catheters are made to withstand the blood pressures, as well as flow pressure for injection and withdrawal of materials and solutions. Such devices may be useful for controlling proximal artery blood pressure, preventing distal ischemia-reperfusion injury, identifying bleeding location, controlling or stopping bleeding at the site of a hemorrhage, repairing and remodeling vascular structures, extending REBOA use duration, and performing fluid resuscitation.

BRIEF DESCRIPTION OF THE DRAWINGS

The numerous advantages of the present invention may be better understood by those skilled in the art by reference to the accompanying figures in which:

FIG. 2 is a side schematic view of a balloon catheter in accordance with further aspects of an embodiment of the invention.

FIG. 3 is a side schematic view of balloon catheter 100 in accordance with further aspects of an embodiment of the invention.

FIG. 6 is a side schematic view of a balloon catheter in accordance with still further aspects of an embodiment of the invention.

FIG. 7 is a side schematic view of the balloon catheter of FIG. 6 having proximal openings positioned between a proximal balloon and a distal balloon.

DETAILED DESCRIPTION OF THE PREFERRED EMBODIMENTS

The invention summarized above may be better understood by referring to the following description, claims, and accompanying drawings. This description of an embodiment, set out below to enable one to practice an implementation of the invention, is not intended to limit the preferred embodiment, but to serve as a particular example thereof Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

Figure 1:
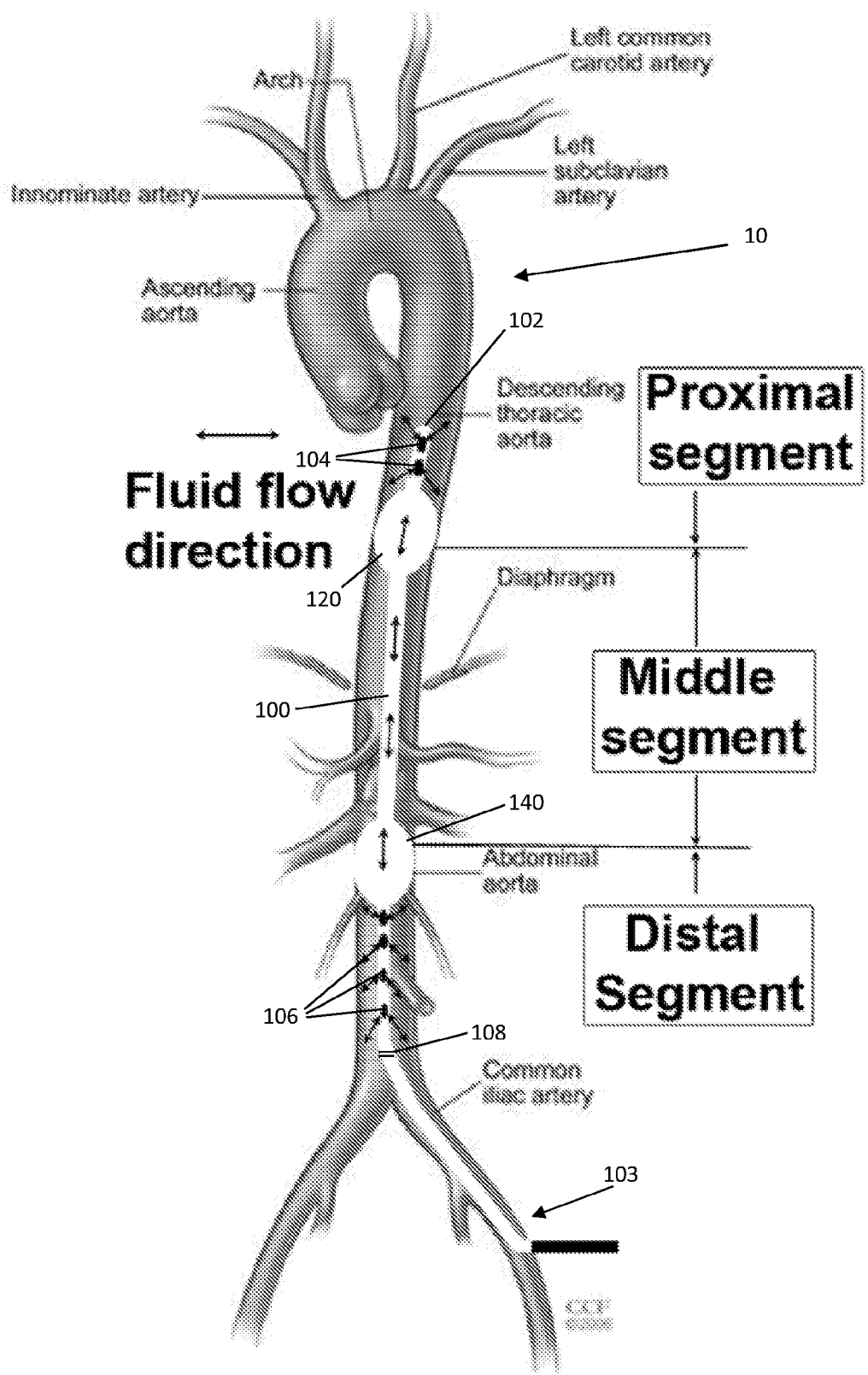
FIG. 1 is a schematic view of a balloon catheter situated within the aorta of a patient in accordance with certain aspects of an embodiment of the invention.

FIG. 1 is a schematic view of a balloon catheter (shown generally at 100) situated within the aorta of a patient (shown generally at 10) in accordance with certain aspects of an embodiment of the invention. As may be seen in FIG. 1, the descending aorta may define three segments: a proximal aorta segment, a middle aorta segment, and a distal aorta segment. Balloon catheter 100 is inserted into the aorta 10 via a femoral artery, and the distal end 102 of balloon catheter 100 is advanced into the proximal segment of the aorta. As used herein, the "distal end" of the balloon catheter 100 refers to the cephalic end that is intended to be advanced into the patient past the site of hemorrhage, and particularly with respect to the exemplary use shown in FIG. 1, into the proximal segment of the patient's aorta. In the exemplary embodiment shown in FIG. 1, balloon catheter 100 carries two balloons—a first balloon 120 closest to the distal end 102 of balloon catheter 100, and a second balloon 140 positioned between the first balloon and the proximal end 103 of balloon catheter 100. When both balloons 120 and 140 are inflated so as to press against the interior vessel wall of the patient's aorta 10, blood flows from the proximal segment of the aorta into inlet openings 104 in balloon catheter 100, through the portion of catheter 100 positioned in the middle segment of the patient's aorta (between the first and second balloons), onward to perfusion openings 106 in balloon catheter 100, and out of perfusion openings 106 into the distal segment of the patient's aorta 10. While FIG. 1 shows a plurality of inlet openings 104 located generally at the distal end of catheter 100, distal end 102 of catheter 100 may alternatively comprise simply an open end forming a single inlet opening 104.

With the foregoing configuration, in the event that the middle segment of aorta 10 is hemorrhaging due to an injury, blood flow is partially or completely blocked to such middle segment, while blood nonetheless continues to flow to the distal segment of aorta 10 through balloon catheter 100.

In an exemplary configuration, the balloon catheter 100 of the current embodiment may have a length of approximately 1 to 2 feet, and a distance between the balloons 120 and 140 may be approximately 4 to 8 inches. However, the balloon catheter 100 may have other lengths and the balloons 120 and 140 may be positioned at different distances (such as may be desirable for use in differing portions of a patient's body or to account for varying physiologies between different types, ages, etc. of patients), as may be readily configured by persons of ordinary skill in the art. Preferably, a flow restricting device, such as a two- or multi-way stopper 108, is positioned within catheter 100 between perfusion ports 106 and the proximal end of catheter 100 so as to allow maximum blood flow to the distal segment of the patient's aorta 10. Such stopper 108 may optionally be opened to allow infusion of medicants or other materials. Thus, stopper 108 may be configured as a solid wall, a one-way valve, or such other catheter flow control device as may be readily selected by persons skilled in the art to meet the requirements of a particular application.

FIG. 2 provides a side schematic view of a balloon catheter (shown generally at 100) in accordance with further aspects of an embodiment of the invention. In the exemplary configuration of FIG. 2, balloon catheter 100 carries two balloons—first balloon 120 closest to the distal end 102 of balloon catheter 100, and second balloon 140 closest to the proximal end 103 of balloon catheter 100. One or more inlet openings 104 are positioned adjacent the distal end 102 of balloon catheter 100, and one or more perfusion openings 106 are positioned toward the proximal end 103 of balloon catheter 100, and more particularly proximal to second balloon 140. Preferably, two- or multi-way stopper 108 is positioned at the proximal end 103 of catheter 100, and proximal to perfusion openings 106, so as to allow maximum blood flow to the distal segment of the patient's aorta 10. In another embodiment, the two- or multi-way stopper 108 is internally positioned within balloon catheter 100. One or more middle segment openings 110 may also be provided in balloon catheter 100 in a middle segment 112 of balloon catheter 100 that extends between first balloon 120 and second balloon 140. Middle segment openings 110 are provided to allow fluids or other materials to flow to the middle segment of a patient's aorta from the proximal end of balloon catheter 100, such as blood, medicants, or other materials.

In certain configurations, at least one of first balloon 120 and second balloon 140 may be movable with respect to balloon catheter 100; for instance, one or both of first balloon 120 and second balloon 140 may have a central channel extending therethrough through which catheter 100 extends, such that either of first balloon 120 or second balloon 140, or both, may be slidable along the exterior of catheter 100, thus allowing adjustment of the relative positions of balloons 120 and 140 for varying patient physiology and condition. In the event that either of first balloon 120 and/or second balloon 140 are to be moveably mounted on the exterior of catheter 100, they are nonetheless configured to provide a fluid-tight seal between the catheter 100 and the central channels of balloons 120 and 140 when the balloons are inflated, thus blocking the flow of blood other than through the interior of catheter 100.

With continued reference to FIG. 2, balloon catheter 100 may comprise a generally circular shaft in cross-section, and may carry multiple, concentric conduits therein, each of which services a portion of balloon catheter 100. More particularly, within the shaft of balloon catheter 100, a first conduit 114 extends through catheter 100 to first balloon 120, and may carry air or other fluid therein to inflate first balloon 120. A second conduit 115, optionally concentrically positioned within first conduit 114, extends through catheter 100 to second balloon 140, and may likewise carry air or other fluid therein to inflate second balloon 140. A third conduit 116, optionally concentrically positioned within second conduit 115, extends through catheter 100 to and is in fluid communication with middle segment openings 110 so as to allow flow of fluids delivered from outside of the patient to the portion of the patient's vascular system that is being treated. Finally, a fourth conduit 117, optionally concentrically positioned within third conduit 116, extends through catheter 100 to and is in fluid communication with inlet openings 104 adjacent distal end 102 of catheter 100, and is likewise in fluid communication with perfusion openings 106, thus allowing isolated fluid flow through catheter 100 between inlet openings 104 and perfusion openings 106.

If configured with such concentric conduits as shown in FIG. 2, preferably only one of first balloon 120 and second balloon 140 is moveable, with such moveable balloon being in fluid communication with first conduit 114 (the other, non-moveable balloon in fluid communication with the other, non-moveable balloon). Thus, outermost first conduit 114 may be moveable with respect to the body of catheter 100 and may thus move with the moveable balloon which it inflates, with a fluid conduit passing from first conduit 114, through the body of catheter 100 and into such moveable balloon. Alternatively, first conduit 114 may be movably mounted on the exterior of the body of catheter 100 so as to avoid the need to pass through the body of catheter 100.

Preferably, pressure sensors 118 and 119 are also provided extending through catheter 100. More particularly, first pressure sensor 118 extends from proximal end 103 of catheter 100 to a position within fourth conduit 117, at which it may measure the pressure adjacent inlet openings 104, and second pressure sensor 119 extends from proximal end 103 of catheter 100 to a position within third conduit 116 at which it may measure the pressure adjacent middle segment openings 110. Such configuration allows an operator to detect a pressure gradient between inlet openings 104 and middle segment openings 110, and position, for example, moveable second balloon 140 so as to maximize that pressure gradient, indicating that the site of the hemorrhage within the patient has been properly isolated from blood flow.

FIG. 3 provides a side schematic view of balloon catheter 100 in accordance with further aspects of an embodiment of the invention. The configuration of FIG. 3 is similar to the configuration shown in FIG. 2, with like elements identified with like reference numerals. However, in the optional configuration presented in FIG. 3, first conduit 114 extending to first balloon 120, second conduit 115 extending to second balloon 140, and third conduit 116 extending to middle segment openings 110 are all arranged parallel to fourth conduit 117 extending to the distal end 102 of catheter 100, instead of being concentrically arranged. Optionally, in the configuration of FIG. 3, all of first conduit 114, second conduit 115, third conduit 116, and fourth conduit 117 may extend in parallel through a circular sleeve (not shown for clarity) that forms the exterior of balloon catheter 100.

Alternatively, first conduit 114 extending to first balloon 120 and second conduit 115 extending to second balloon 140 may extend along the exterior of the body of catheter 100, so as to avoid the need for air channels to extend through the wall of the body of catheter 100.

Such configuration will also aid in allowing one or both of first balloon 120 and second balloon 140 to be moveable with respect to the body of catheter 100. By way of non-limiting example, either or both of first conduit 114 and second conduit 115 may extend from the proximal end 103 of catheter 100 along the exterior of the body of catheter 100 (in the event that the balloon to which such first conduit 114 or second conduit 115 attaches is fixed), or may be moveably mounted on the exterior of catheter 100 (in the event that the balloon to which such first conduit 114 or second conduit 115 attaches is moveable). In the case of such a moveable mounting, first conduit 114 and second conduit 115 may for instance extend through channels, loops, clips, or any other holding assembly as may occur to those skilled in the art that allows movement of the respective conduit 114 or 115 with respect to catheter 100 without detachment therefrom.

Figure 4:
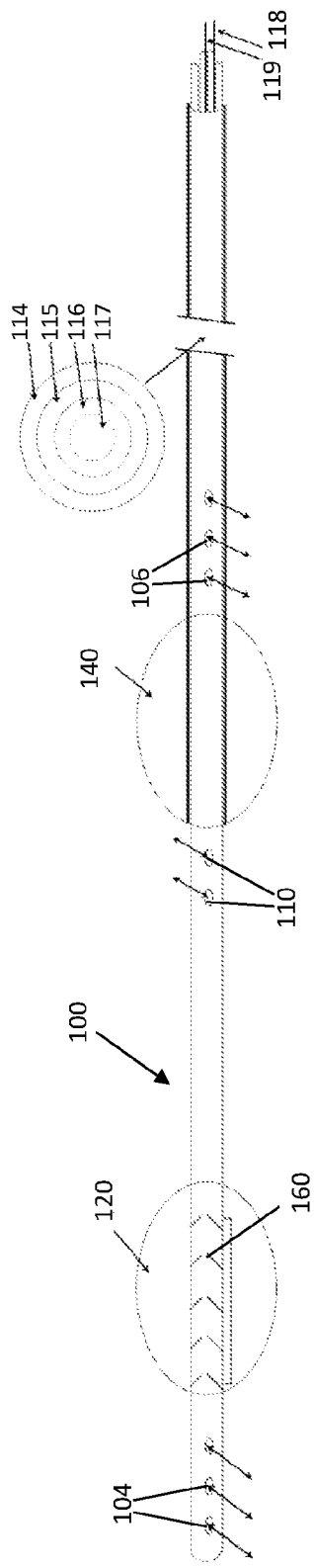
FIG. 4 is a side schematic view of the balloon catheter 100 of FIG. 2 including an in-line flow restrictor.
Figure 5:
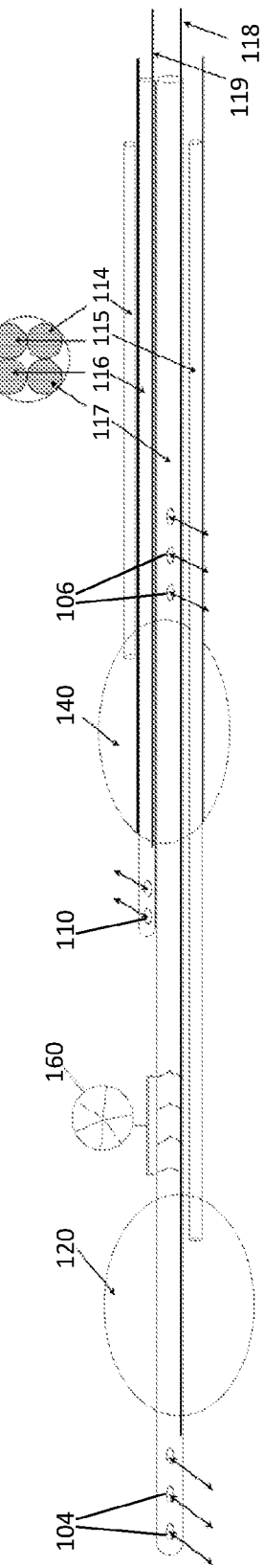
FIG. 5 is a side schematic view of the balloon catheter 100 of FIG. 3 including an in-line flow restrictor.

Next, FIG. 4 provides a side schematic view of the balloon catheter 100 of FIG. 2, and FIG. 5 provides a side schematic view of the balloon catheter 100 of FIG. 3, each with the additional feature of an in-line flow restrictor 160 positioned within balloon catheter 100, and more particularly within fourth conduit 117 that is in fluid communication with inlet openings 104 and perfusion openings 106. Flow restrictor 160 may comprise, by way of non-limiting example, a manually operable pressure valve, porous materials, single or multiple layer nets, filters or filtering materials, and the like, all of which constructions are known to those skilled in the art, and all of which may reduce the pressure in the distal segment of the patient's artery (i.e., the portion in fluid communication with catheter openings 106), or create a pressure gradient between the proximal segment and distal segment of the patient's artery, where such a pressure gradient is desirable. For example, a pressure gradient between the proximal segment and distal segment of the patient's artery of 100 mmHg may control hemorrhaging.

Next, FIG. 6 provides a side schematic view of a balloon catheter 100 in accordance with still further aspects of an embodiment of the invention. In the configuration of FIG. 6, balloon catheter 100 again carries two balloons—first balloon 120 closest to the distal end 102 of balloon catheter 100, and second balloon 140 furthest from the distal end 102 of balloon catheter 100. Once again, first balloon 120 and/or second balloon 140 may be movable with respect to one another, such as by making one of first balloon 120 and second balloon 140 slidable along the exterior of balloon catheter 100. Inlet openings 104 are positioned adjacent the distal end 102 of balloon catheter 100, and perfusion openings 106 are positioned toward the proximal end 103 of balloon catheter 100, and more particularly proximal to second balloon 140. A first conduit 114 extends from the proximal end 103 of catheter 100 to first balloon 120, and may carry air or other fluid therein to inflate first balloon 120. A second conduit 115 extends from the proximal end 103 of catheter 100 to second balloon 140, and may likewise carry air or other fluid therein to inflate second balloon 140. A third conduit 116 extends through catheter 100 to and is in fluid communication with perfusion openings 106, and a fourth conduit 117 extends through catheter 100 to and is in fluid communication with inlet openings 104 adjacent distal end 102 of catheter 100. The proximal ends of each of third conduit 116 and fourth conduit 117 are joined to and in fluid communication with an external pressure control valve 170 positioned outside of the patient's body, which external pressure control valve 170 is configured to regulate flow of blood from inlet openings 104 to perfusion openings 106. This configuration allows isolated fluid flow through catheter 100 between inlet openings 104 and perfusion openings 106, while regulating the flow through pressure control valve 170 allows improved control of the patient's blood pressure adjacent the distal end 102 of balloon catheter 100, and likewise controlled pressure change at the proximal end 103 of balloon catheter 100 after repair of the hemorrhaging artery so as to minimize the risk of complications resulting from distal ischemia-reperfusion and rebound hypotension upon deflation of the balloons 120 and 140.

In the configuration shown in FIG. 6, conduits 114, 115, 116 and 117 may be arranged in parallel and extend within the hollow interior shaft of catheter 100, or air delivery conduits 114 and 115 may be arranged on the exterior of catheter 100, all as explained in detail above.

FIG. 7 shows the balloon catheter 100 of FIG. 6, but in this configuration having perfusion openings 106 positioned between first balloon 120 and second balloon 140. In this configuration, blood flow from the inlet openings 104 of balloon catheter 100, and thus from the proximal segment of the patient's aorta, to the middle segment of the patient's aorta may be regulated so as to provide blood supply to such middle segment, when necessary. Blood flow to the distal segment of the patient's aorta and beyond may then be regulated through a combination of controlling flow through control valve 170 and inflation and deflation of second balloon 140.

Figure 8:
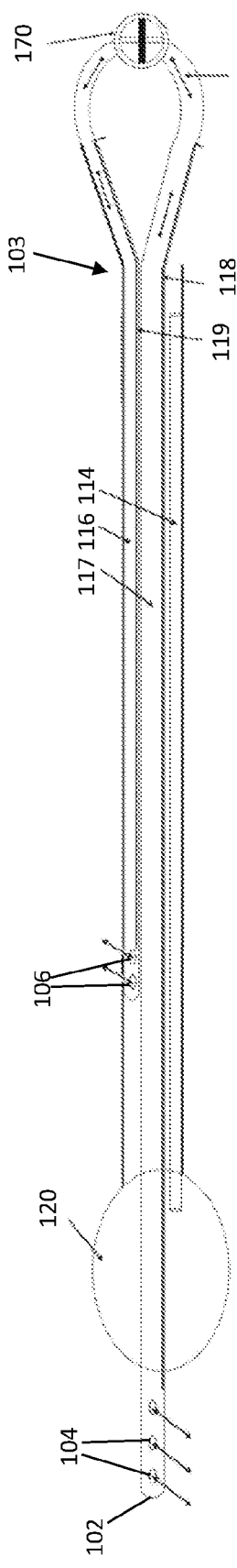
FIG. 8 is a side schematic view of the balloon catheter of FIG. 6 having only a single proximal balloon.

FIG. 8 shows the balloon catheter 100 of FIG. 6, but in this configuration, only a single balloon 120 is provided. In this configuration, blood flow from the inlet openings 104 adjacent distal end 102 of balloon catheter 100, and thus from the proximal segment of the patient's aorta, to both the middle segment and distal segment of the patient's aorta and beyond may be regulated solely through control valve 170, allowing the operator to control the flow at the start of repair of the hemorrhage, change flow during and after the repair, and ultimately allow full flow when the repair is believed to have been completed, all while maintaining balloon 120 in place in the event that such repair fails or leaks are discovered after the corrective surgery.

Figure 9:
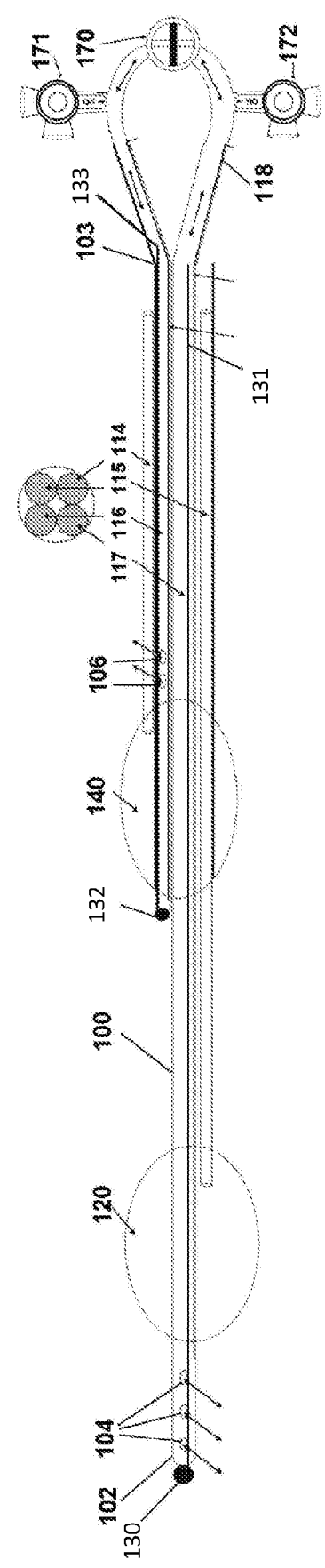
FIG. 9 is an illustration of balloon catheter 100 including a camera and probe.

Each of the foregoing configurations of balloon catheter 100 may also include at least one of a camera 130 or a blood flow scan probe 132 configured to view the area adjacent distal end 102 or the area around perfusion openings 106 of catheter 100, as shown in FIG. 9.

Such configuration of balloon catheter 100 with camera 130 allows an operator to use ultrasound imaging techniques to create real-time endovascular images of arteries, although other techniques may likewise be used. Another configuration of balloon catheter 100, which may include blood flow probe 132, preferably includes a laser Doppler ultrasound probe. In each such configuration, the signals from the camera 130 and/or blood flow probe 132 are transmitted via a camera cable 131 or probe cable 133, respectively, to an external monitor. Thus, blood flow and endovascular conditions can be monitored using at least one of the camera 130 or probe 132.

With continued reference to FIG. 9, balloon catheter 100 may also include one or more ports 171 and 172 that fluidly engage the blood-carrying conduits of catheter 100 for injection or withdrawal of blood and any materials or solutions. Such materials or solutions may include contrast materials, also called contrast agents or contrast media for improving images of the inside of the body produced by x-rays, computed tomography (CT), radiography, fluoroscopy, magnetic resonance (MR) imaging, ultrasound, or any other methods. Often, contrast materials allow an operator to distinguish normal from abnormal conditions.

Figure 10:
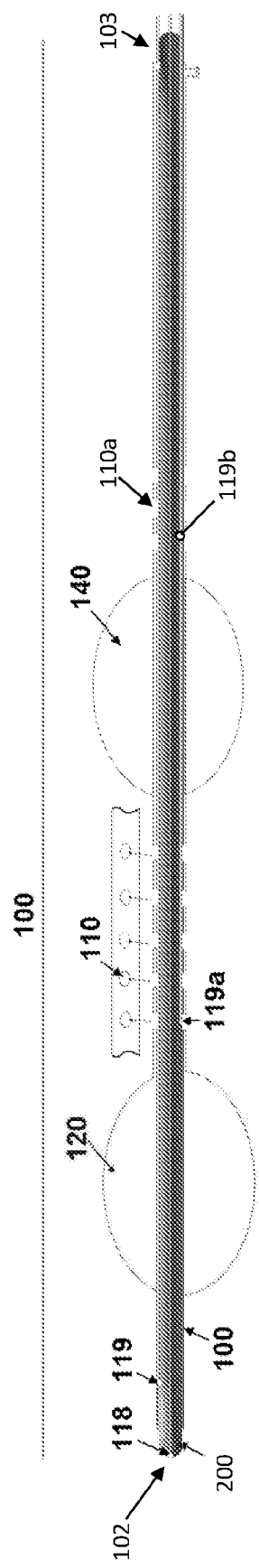
FIG. 10 is a side schematic view of balloon catheter 100 in accordance with still further aspects of an embodiment of the invention.

In accordance with still further aspects of an embodiment of the invention, and with reference to FIG. 10, balloon catheter 100 may be equipped with an internally moveable member 200, which may be in the form of a plunger or piston (similar in configuration to the plunger of a syringe). The tip of moveable member 200 fits tightly within the cylindrical interior of balloon catheter 100. Internally moveable member 200 controls the blood flow through catheter 100, and thus the blood flow from the distal end 102 of catheter 100 and into the patient's vessel through one or more perfusion openings 110 in catheter 100 on an opposite side of balloon 120 from distal end 102. Preferably three pressure or blood flow sensors are provided. More particularly, pressure sensor 118 may be affixed to a distal end of moveable member 200, and is configured to measure blood pressure at the tip of moveable member 200. Likewise, pressure sensor 119 may be affixed to the interior of catheter 100 between distal end 102 of catheter 100 and balloon 120, and is configured to measure blood pressure inside of catheter 100. Finally, pressure sensor 119a may be affixed to the interior of catheter 100 adjacent one or more perfusion openings 110 (i.e., on an opposite side of balloon 120 from distal end 102), and is configured to measure blood pressure at perfusion openings 110. Such combination of sensors 118, 119, and 119a are positioned to monitor and control, via movement of moveable member 200, the blood flow rate between proximal and distal regions of the patient's vessel being treated, such as by way of non-limiting example between the proximal and distal portions of the patient's aorta for performing partial REBOA. In this case of performing partial REBOA, balloon catheter 100 is advanced into the patient's descending aorta. Withdrawing or pushing moveable member 200 along the inner lumen of catheter 100 (in combination with inflation of balloon 120) guides the blood flow from the proximal region of the patient's aorta to the distal region of the patient's aorta. The blood pressures or blood flow gradients, or different readings among sensors 118, 119, and 119a serve as surrogate markers of partial REBOA. The moveable member 200 may be made or coated with materials including but not limited to contrast materials (also called contrast agents or contrast media) for improving images of the inside of the body produced by x-rays, computed tomography (CT), radiography, fluoroscopy, magnetic resonance (MR) imaging, ultrasound, or any other methods.

In the configuration shown in FIG. 10, second moveable balloon 140 may optionally be provided, and may be used to create a blood flow in the patient's vessel adjacent distal end 102 of catheter 100 to perfusion openings 110a located between second balloon 140 and proximal end 103 of catheter 100, thus avoiding blood flow to the hemorrhage site between balloons 120 and 140. In an exemplary configuration, perfusion openings 110 may not be present, with perfusion openings 110a located between second balloon 140 and proximal end 103 of catheter 100. In another exemplary configuration, perfusion openings 110 may be provided in catheter 100 between first balloon 120 and second balloon 140, in addition to perfusion openings 110a being provided between second balloon 140 and proximal end 103 of catheter 100. In this configuration that includes both perfusion openings 110 and 110a, optionally moveable member 200 may itself comprise a hollow conduit, inside of which is positioned yet another moveable member in the form of a second plunger or moveable stopper. This configuration allows progressive, controlled blood flow to perfusion openings 110a (through movement of the inner-most plunger or moveable stopper), and to perfusion openings 110 (through movement of outer portion of moveable member 200). Moreover, in the event that perfusion openings 110a are provided between second balloon 140 and proximal end 103, and additional pressure sensor 119b may be mounted to the interior of catheter 100 adjacent perfusion openings 110a configured to measure blood pressure at perfusion openings 110a, thus helping to ensure that an adequate blood supply is provided to the distal segment of the patient's aorta or other vessel being treated.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It should be understood, therefore, that the invention may be practiced otherwise than as specifically set forth herein.

What is claimed is:

1. A balloon catheter flow device, comprising:
   a catheter having a distal end and a proximal end opposite said distal end;
   a first inflatable balloon positioned on said catheter;
   at least one fluid inlet opening in a wall of the catheter allowing fluid communication between an interior and an exterior of said catheter, said fluid inlet opening positioned between said first inflatable balloon and said distal end of said catheter;
   at least one fluid perfusion opening in the wall of the catheter allowing fluid communication between an interior and an exterior of said catheter, said fluid perfusion opening positioned between said first inflatable balloon and said proximal end of said catheter; and
   a first closed fluid flow channel extending between said at least one fluid inlet opening and said at least one fluid perfusion opening such that said at least one fluid inlet opening is in fluid communication with said at least one fluid perfusion opening, and wherein said balloon catheter flow device is configured to transfer fluid from a first portion of a patient's vessel that is distal to said at least one fluid inlet opening, through said at least one fluid inlet, and out from said at least one fluid perfusion opening to a second portion of the patient's vessel that is proximal to said at least one fluid perfusion opening.

2. The balloon catheter flow device of claim 1, further comprising a second inflatable balloon positioned on said catheter between said first inflatable balloon and said proximal end of said catheter.

3. The balloon catheter flow device of claim 2, wherein said second inflatable balloon is positioned between said first inflatable balloon and said at least one perfusion fluid opening.

4. The balloon catheter flow device of claim 3, further comprising a second closed fluid flow channel extending from said proximal end of said catheter to a position between said first inflatable balloon and said second inflatable balloon, said second closed fluid flow channel having at least one mid-segment fluid opening allowing fluid communication between an interior of said second closed fluid flow channel and a volume outside of said balloon catheter between said first inflatable balloon and said second inflatable balloon.

5. The balloon catheter flow device of claim 2, wherein each of said first inflatable balloon and said second inflatable balloon are independently inflatable.

6. The balloon catheter flow device of claim 2, wherein said second inflatable balloon is moveable along said catheter.

7. The balloon catheter flow device of claim 1, further comprising a flow restrictor positioned within said catheter.

8. The balloon catheter flow device of claim 7, wherein said flow restrictor is positioned between said at least one inlet fluid opening and said at least one perfusion fluid opening.

9. The balloon catheter flow device of claim 1, further comprising a valve intercepting said catheter between said distal end and said proximal end and operable to control fluid flow from said at least one inlet fluid opening to said at least one perfusion fluid opening.

10. The balloon catheter flow device of claim 9, wherein said valve is positioned on said balloon catheter flow device so as to remain outside of a patient's body when said at least one inlet fluid opening and said at least one perfusion fluid opening are both positioned within the patient's body.

11. The balloon catheter flow device of claim 1, further comprising a plunger moveably mounted within said catheter.

12. The balloon catheter flow device of claim 11, further comprising a second inflatable balloon positioned on said catheter between said perfusion opening and said proximal end of said catheter.

13. The balloon catheter flow device of claim 12, further comprising at least one second perfusion opening in said catheter between said second balloon and said proximal end of said catheter.

14. The balloon catheter flow device of claim 13, wherein said second balloon is movably positioned on said catheter.

15. The balloon catheter flow device of claim 11, further comprising a pressure sensor mounted to a distal end of said plunger.

16. The balloon catheter flow device of claim 15, further comprising a pressure sensor affixed to an interior of said catheter adjacent said perfusion opening.

17. The balloon catheter flow device of claim 16, further comprising a pressure sensor affixed to an interior of said catheter adjacent said distal end of said catheter.

18. A method for regulating blood flow within a patient's hemorrhaging vessel, comprising the steps of:
   providing a balloon catheter flow device, said balloon catheter flow device further comprising:
   a catheter having a distal end and a proximal end opposite said distal end;
   a first inflatable balloon positioned on said catheter;
   at least one fluid inlet opening in a wall of the catheter allowing fluid communication between an interior and an exterior of said catheter, said fluid inlet opening positioned between said first inflatable balloon and said distal end of said catheter;
   at least one fluid perfusion opening in the wall of the catheter allowing fluid communication between an interior and an exterior of said catheter, said fluid perfusion opening positioned between said first inflatable balloon and said proximal end of said catheter; and
   a first closed fluid flow channel extending between said at least one fluid inlet opening and said at least one fluid perfusion opening such that said at least one fluid inlet opening is in fluid communication with said at least one fluid perfusion opening, and wherein said balloon catheter flow device is configured to transfer fluid from a first portion of a patient's vessel that is distal to said at least one fluid inlet opening, through said at least one fluid inlet, and out from said at least one fluid perfusion opening to a second portion of the patient's vessel that is proximal to said at least one fluid perfusion opening;

advancing said distal end of said balloon catheter flow device into a patient's hemorrhaging blood vessel;

inflating said first inflatable balloon to prevent flow through the patient's vessel other than through said catheter from said at least one fluid inlet opening to said at least one fluid perfusion opening; and regulating blood flow through said balloon catheter flow device to reduce blood flow to a site of hemorrhage in said patient's blood vessel while allowing blood flow to a distal segment of said patient's blood vessel located past said site of hemorrhage.

19. The method of claim 18, wherein said balloon catheter flow device further comprises a plunger moveably mounted within said catheter.

20. The method of claim 19, wherein said step of regulating blood flow further comprises moving said plunger to gradually enable blood flow through said perfusion port.

\* \* \* \* \*